(12) United States Patent
Lee et al.

(10) Patent No.: US 10,252,080 B2
(45) Date of Patent: Apr. 9, 2019

(54) DISPLAY DEVICE AND DISPLAY SYSTEM INCLUDING FIRST POLARIZATION LAYER FORMED OVER FIRST DISPLAY AREA AND SECOND POLARIZATION LAYER FORMED OVER SECOND DISPLAY AREA

(71) Applicant: Samsung Display Co., Ltd., Yongin (KR)

(72) Inventors: Changhoon Lee, Yongin (KR); Jongsung Bae, Yongin (KR); Jongin Baek, Yongin (KR); Yijoon Ahn, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 14/721,319

(22) Filed: May 26, 2015

(65) Prior Publication Data

US 2016/0096038 A1 Apr. 7, 2016

(30) Foreign Application Priority Data

Oct. 6, 2014 (KR) .................... 10-2014-0134484

(51) Int. Cl.
*A61N 5/06* (2006.01)
*G02B 27/26* (2006.01)
(Continued)

(52) U.S. Cl.
CPC .......... *A61N 5/0618* (2013.01); *A61N 5/0616* (2013.01); *G02B 27/26* (2013.01); *G09G 5/02* (2013.01); *A61N 2005/0626* (2013.01); *A61N 2005/0648* (2013.01); *A61N 2005/0659* (2013.01); *A61N 2005/0661* (2013.01); *A61N 2005/0663* (2013.01); *A61N 2005/073* (2013.01); *G09G 3/001* (2013.01); *G09G 2320/0666* (2013.01); *G09G 2340/06* (2013.01)

(58) Field of Classification Search
CPC ... A61N 2005/0626; A61N 2005/0648; G09G 5/02; G09G 2320/0666
See application file for complete search history.

(56) References Cited

U.S. PATENT DOCUMENTS

| | | | |
|---|---|---|---|
| 7,812,366 B1 * | 10/2010 | Sampath ................ | B82Y 20/00 257/103 |
| 2005/0134800 A1 * | 6/2005 | Kim ........................ | H04N 9/68 351/242 |

(Continued)

FOREIGN PATENT DOCUMENTS

KR 10-2015-0020870 A 2/2015

*Primary Examiner* — Chun-Nan Lin
(74) *Attorney, Agent, or Firm* — Lewis Roca Rothgerber Christie LLP (57) ABSTRACT

A display device and a display system are disclosed. In one aspect, the display device includes a pixel unit including a first display area and a second display area, a controller configured to control the pixel unit to display a first image in the first display area and a second image in the second display area, a first polarization layer formed over the first display area and having a first polarization direction, and a second polarization layer formed over the second display area and having a second polarization direction different from the first polarization direction. The second image includes a light therapy image or an image adjusted for color blindness.

17 Claims, 7 Drawing Sheets

(51) Int. Cl.
   *G09G 5/02*         (2006.01)
   *A61N 5/073*         (2006.01)
   *G09G 3/00*          (2006.01)

(56) References Cited

U.S. PATENT DOCUMENTS

| | | | |
|---|---|---|---|
| 2007/0063961 A1* | 3/2007 | Kuroki | G09G 3/3413 |
| | | | 345/102 |
| 2009/0059145 A1* | 3/2009 | Nishioka | G02F 1/133707 |
| | | | 349/119 |
| 2009/0143842 A1 | 6/2009 | Cumbie et al. | |
| 2010/0283969 A1 | 11/2010 | Cooperstock et al. | |
| 2011/0025832 A1* | 2/2011 | Cowan | G02B 27/0018 |
| | | | 348/51 |
| 2011/0050547 A1* | 3/2011 | Mukawa | G02B 27/0176 |
| | | | 345/8 |
| 2011/0164122 A1 | 7/2011 | Hardacker | |
| 2012/0081412 A1* | 4/2012 | Kim | G06F 3/0421 |
| | | | 345/690 |
| 2012/0147281 A1* | 6/2012 | Matsuhiro | G02B 27/26 |
| | | | 349/15 |
| 2012/0268356 A1* | 10/2012 | Kim | G02F 1/13338 |
| | | | 345/84 |
| 2012/0320044 A1* | 12/2012 | Tsai | G02B 27/2264 |
| | | | 345/419 |
| 2015/0051672 A1 | 2/2015 | Jo et al. | |
| 2015/0302773 A1* | 10/2015 | Stone | G02B 6/0035 |
| | | | 348/63 |
| 2016/0104453 A1* | 4/2016 | Borenstein | G09G 5/02 |
| | | | 348/62 |

* cited by examiner

DISPLAY DEVICE AND DISPLAY SYSTEM INCLUDING FIRST POLARIZATION LAYER FORMED OVER FIRST DISPLAY AREA AND SECOND POLARIZATION LAYER FORMED OVER SECOND DISPLAY AREA

RELATED APPLICATION

This application claims the benefit of Korean Patent Application No. 10-2014-0134484, filed on Oct. 6, 2014, in the Korean Intellectual Property Office, the disclosure of which is incorporated herein in its entirety by reference.

BACKGROUND

Field

The described technology generally relates to a display device and a display system.

Description of the Related Technology

A light therapy image, which is effective for skin care or controlling biorhythms, includes light having a wavelength in the infrared range or the blue wavelength range. If skin is exposed to the light as described above, it can be beneficial to the skin.

SUMMARY OF CERTAIN INVENTIVE ASPECTS

One inventive aspect is a display device whereby a user can view an information image on a display and receive light therapy at the same time.

Another aspect is a display device, a light therapy image of which does not affect the eyes of a display user.

Another aspect is a display device, images of which can be viewed by those who are color blind and those who are not color blind at the same time.

Another aspect is a display device that includes: a pixel unit that includes a first display area and a second display area; a control unit that controls the pixel unit such that a first image is displayed on the first display area and a second image is displayed on the second display area; a first polarization layer that is attached to the first display area and has a first polarization direction; and a second polarization layer that is attached to the second display area and has a second polarization direction that is different from the first polarization direction, wherein the second image is a light therapy image or an image adjusted for color blindness.

The pixel unit can include a plurality of pixel lines that each include a plurality of pixels, wherein the first display area includes one of a first area in which odd-numbered pixel lines of the pixel unit are located and a second area in which even-numbered pixel lines of the pixel unit are located, and the second display area includes the other of the first area and the second area.

If the second image is the light therapy image, the control unit can control the pixel unit such that at least one of light having a peak energy in an infrared range, light having a peak energy in an ultraviolet range, and light having a peak energy in a blue wavelength range is emitted through the second display area.

If the second image is the light therapy image, the control unit can control the pixel unit such that at least one of light that is beneficial to skin care, light that is beneficial to biorhythm control, light that is beneficial to depression treatment, light that is beneficial to inflammation treatment, and light that is beneficial to treatment of cancer is emitted through the second display area.

The display device can further include an information image signal generating unit that generates a first image signal based on an input image signal received from outside the display device, wherein the first image signal is a signal for displaying the first image on the first display area.

The information image signal generating unit can generate the first image signal based on a proportion of the first display area with respect to the pixel unit.

The information image signal generating unit can generate the image signal based on a resolution of the first display area.

The display device can further include a image signal generating unit for color blindness that generates a second image signal based on at least one of the input image signal and the first image signal, wherein the second image signal is a signal for displaying the second image on the second display area.

The second image can be an image in which at least one color among red, green, and blue is emphasized compared to the remaining colors based on whether a user of the display device is color blind.

The first polarization direction can be one of a right-handed circular polarization direction and a left-handed circular polarization direction, and the second polarization direction can be the other of the right-handed circular polarization direction and the left-handed circular polarization direction.

The display device can further include a sensing unit that senses a tilt angle of the head of a user with respect to the display device, wherein the first polarization direction is a first linear polarization direction, and the second polarization direction is a second linear polarization direction that is orthogonal to the first linear polarization direction.

The display device can further include an image signal correcting unit that corrects a first image signal and a second image signal based on the tilt angle of the head of the user, wherein the first image signal is for displaying the first image on the first display area, and the second image signal is for displaying the second image on the second display area.

The second image can be a light therapy image, and the image signal correcting unit can correct the first image signal such that luminance of light emitted by each pixel of the first display area increases as the tilt angle of the user's head increases.

The second image can be a light therapy image, and the image signal correcting unit can correct the second image signal such that the second image is not emitted through the second display area if the tilt angle of the user's head exceeds a critical angle.

Another aspect is a display system that includes: the display device described above; and a first eyeglass device, wherein a left lens and a right lens of the first eyeglass device include a third polarization layer having a third polarization direction.

The second image can be a light therapy image, and the third polarization direction is the same as the first polarization direction, and light emitted through the second display area does not enter eyes of a user who is wearing the first eyeglass device.

The display system can further include a second eyeglass device, wherein a left lens and a right lens of the second eyeglass device include a fourth polarization layer having a fourth polarization direction, and the second image is an image adjusted for color blindness, and the third polarization direction is the same as the first polarization direction, so that light emitted through the second display area does not enter eyes of a user who is wearing the first eyeglass device, and the fourth polarization direction is the same as the second polarization direction, and light emitted through the first display area does not enter eyes of a user who is wearing the second eyeglass device.

Another aspect is a display device comprising a pixel unit including a first display area and a second display area, a controller configured to control the pixel unit to display a first image in the first display area and a second image in the second display area, a first polarization layer formed over the first display area and having a first polarization direction, and a second polarization layer formed over the second display area and having a second polarization direction different from the first polarization direction, wherein the second image includes a light therapy image or an image adjusted for color blindness.

In the above display device, the pixel unit comprises a plurality of pixel lines including odd-numbered and even-numbered pixel lines, wherein each pixel line includes a plurality of pixels, wherein the first display area comprises one of a first area where the odd-numbered pixel lines are located and a second area where the even-numbered pixel lines are located, and wherein the second display area comprises the other of the first area and the second area.

In the above display device, if the second image is the light therapy image, the controller is further configured to control the pixel unit to emit light having peak energy in one of an infrared range, an ultraviolet range, and a blue wavelength range through the second display area.

In the above display device, if the second image is the light therapy image, the controller is further configured to control the pixel unit to emit light that is configured to at least partially treat at least one of skin trouble, abnormal biorhythm, depression, inflammation, and cancer through the second display area.

In the above display device, the controller comprises an information image signal generator configured to generate a first image signal based at least in part on an input image signal received from an external device, wherein the pixel unit is further configured to display the first image based on the first image signal.

In the above display device, the information image signal generator is further configured to generate the first image signal based at least in part on a ratio of the first display area to the area of the pixel unit.

In the above display device, the information image signal generator is further configured to generate the first image signal based at least in part on a resolution of the first display area.

The above display device further comprises a color blindness image signal generator configured to generate a second image signal based at least in part on at least one of the input image signal and the first image signal, wherein the pixel unit is further configured to display the second image based on the second image signal.

In the above display device, the second image includes an image in which at least one of green, red and blue colors is emphasized compared to the remaining color(s) based at least in part on whether a user of the display device is color blind.

In the above display device, the first polarization direction is one of a right-handed circular polarization direction and a left-handed circular polarization direction, wherein the second polarization direction is the other circular polarization direction.

The above display device further comprises a sensor configured to sense a tilt angle of the head of a user with respect to the display device, wherein the first polarization direction is a first linear polarization direction, and wherein the second polarization direction is a second linear polarization direction substantially orthogonal to the first linear polarization direction.

The above display device further comprises an image signal corrector configured to correct first and second image signals based at least in part on the tilt angle, wherein the pixel unit is further configured to respectively display the first and second images based on the first and second image signals.

In the above display device, when the second image includes the light therapy image, the image signal corrector is further configured to increase the luminance of light emitted by each pixel in the first display area as the tilt angle increases.

In the above display device, when the second image includes the light therapy image, the image signal corrector is further configured to block the second image signal such that the second image is not emitted through the second display area if the tilt angle exceeds a critical angle.

Another aspect is a display system comprising a display device. The display device comprises a pixel unit including a first display area and a second display area, a controller configured to control the pixel unit to display a first image in the first display area and a second image in the second display area, a first polarization layer formed over the first display area and having a first polarization direction, and a second polarization layer formed over the second display area and having a second polarization direction different from the first polarization direction, wherein the second image includes a light therapy image or an image adjusted for color blindness. The display system also comprises a first eyeglass device comprising left and right lenses, wherein each of the left right lenses comprises a third polarization layer having a third polarization direction.

In the above display system, the second image includes a light therapy image, wherein the third polarization direction is the same as the first polarization direction, and wherein the controller is further configured to control the pixel unit such that light emitted from the second display area does not enter the eyes of a user wearing the first eyeglass device.

The above display system further comprises a second eyeglass device comprising left and right lenses, wherein each of the left and right lenses of the second eyeglass device comprise a fourth polarization layer having a fourth polarization direction, wherein the second image is an image adjusted for color blindness, wherein the third polarization direction is the same as the first polarization direction, wherein the controller is further configured to control the pixel unit such that light emitted from the second display area does not enter eyes of a user wearing the first eyeglass device, and wherein the fourth polarization direction is the same as the second polarization direction, and wherein the controller is further configured to control the pixel unit such that light emitted from the first display area does not enter the eyes of a user wearing the second eyeglass device.

Another aspect is a display device comprising a display panel including odd-numbered and even-numbered pixel lines each comprising a plurality of pixels, wherein the display panel is configured to display a first image through the odd-numbered pixel lines and a second image through the even-numbered pixel lines. The display device also comprises a controller comprising an information image signal generator configured to generate a first image signal based at least in part on an input image signal received from an external device, wherein the display panel is further configured to display the first image based on the first image signal. The display device further comprises a first polarization layer formed over the odd-numbered pixel lines and having a first polarization direction and a second polarization layer formed over the even-numbered pixel lines and having a second polarization direction different from the first polarization direction, wherein the second image includes a light therapy image or an image adjusted for color blindness.

In the above display device, if the second image is the light therapy image, the display panel is further configured to emit light having peak energy in one of an infrared range, an ultraviolet range, and a blue wavelength range through the second display area, and wherein if the second image is the light therapy image, the display panel is further configured to emit light that is configured to at least partially treat at least one of skin trouble, abnormal biorhythm, depression, inflammation, and cancer through the second display area.

The above display device further comprises a sensor configured to sense a tilt angle of the head of a user with respect to the display device, wherein the first polarization direction is a first linear polarization direction, wherein the second polarization direction is a second linear polarization direction substantially orthogonal to the first linear polarization direction, and wherein the controller further comprises an image signal corrector configured to correct the first and second image signals based at least in part on the tilt angle.

These general and specific embodiments can be implemented by using a system, a method, a computer program, or a combination of the system, the method, and the computer program.

DETAILED DESCRIPTION OF CERTAIN INVENTIVE EMBODIMENTS

If human eyes are exposed to a light therapy image used for skin care, harm to optical tissue can occur. Also, images for the color blind and the normally sighted are output differently. Thus, it is difficult for those two populations to view a display at the same time.

Reference will now be made in detail to embodiments, examples of which are illustrated in the accompanying drawings, wherein like reference numerals refer to like elements throughout. In this regard, the present embodiments can have different forms and should not be construed as being limited to the descriptions set forth herein. Accordingly, the embodiments are merely described below, by referring to the figures, to explain aspects of the present description. Expressions such as "at least one of" when preceding a list of elements, modify the entire list of elements and do not modify the individual elements of the list.

As the described technology allows for various changes and numerous embodiments, particular embodiments will be illustrated in the drawings and described in detail in the written description. Hereinafter, effects and features of the present described technology and a method for accomplishing them will be described more fully with reference to the accompanying drawings, in which exemplary embodiments of the described technology are shown. This described technology can, however, be embodied in many different forms and should not be construed as limited to the exemplary embodiments set forth herein.

One or more embodiments of the described technology will be described below in more detail with reference to the accompanying drawing's. Those components that are the same or are in correspondence are rendered the same reference numeral regardless of the figure number, and redundant explanations are omitted.

It will be understood that although the terms "first", "second", etc. can be used herein to describe various components, these components should not be limited by these terms. These components are only used to distinguish one component from another. As used herein, the singular forms "a", "an", and "the" are intended to include the plural forms as well, unless the context clearly indicates otherwise. The use of the terms "a" and "an" and "the" and similar referents in the context of describing the described technology (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein.

Finally, the steps of all methods described herein can be performed in any suitable order unless otherwise indicated herein or otherwise clearly contradicted by context. The use of any and all examples, or exemplary language (e.g., "such as") provided herein, is intended merely to better illuminate the described technology and does not pose a limitation on the scope of the described technology unless otherwise claimed. Numerous modifications and adaptations will be readily apparent to those skilled in this art without departing from the spirit and scope of the present described technology. In this disclosure, the term "substantially" includes the meanings of completely, almost completely or to any significant degree under some applications and in accordance with those skilled in the art. Moreover, "formed on" can also mean "formed over." The term "connected" can include an electrical connection.

Figure 1:
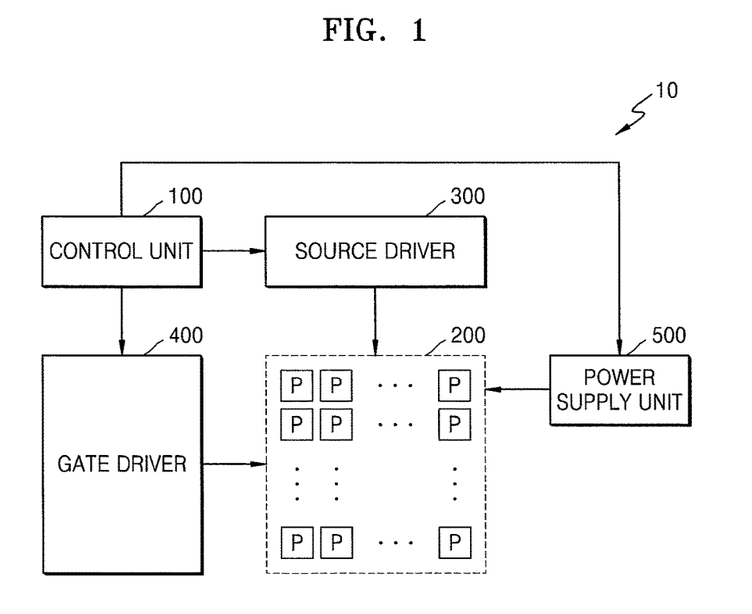
FIG. 1 is a schematic block diagram illustrating a display device according to an embodiment.

FIG. 1 is a schematic block diagram illustrating a display device 10 according to an embodiment.

Referring to FIG. 1, the display device 10 includes a control unit or controller 100, a display unit or display panel 200, a source driver 300, a gate driver 400, and a power supply unit 500.

The display device 10 can be a flat panel display device such as an organic light-emitting diode (OLED) display, a thin film transistor-liquid crystal display (TFT-LCD), a plasma display panel (PDP) or a light-emitting diode (LED) display, but is not limited thereto, and can be various apparatuses that receive an image signal and display an image corresponding to the image signal. The display device 10 can be an electronic device such as a smartphone, a tablet computer, a laptop computer, a monitor, or a TV or an image-displaying component of these electronic devices.

The control unit 100 receives an input image signal from the outside and transmits an output image signal needed to display an image indicated by the input image signal via the display unit 200. The control unit 100 can output a signal for controlling the display unit 200, the source driver 300, the gate driver 400, and the power supply unit 500.

The input image signal is received from the outside of the display device 10. The input image signal includes information for generating an image of a visible range that can be perceived by human's eyes through the display device 10. The input image signal can be a digital signal or an analog signal.

An output signal is needed to display an image indicated by an input image signal. The output signal can include an output image signal obtained by applying a signal processing technique to the input image signal. The output signal can include various signals needed to display a predetermined image via the display unit 200.

Operations of the control unit 100 to generate and transmit an output signal from an input image signal will be described in detail with reference to FIGS. 4, 5, and 7.

The display unit 200 receives a data voltage and displays an image corresponding to the data voltage. The display unit 200 can be a flat panel display panel such as an OLED display panel or a LCD panel. However, the exemplary embodiment is not limited thereto.

The display unit 200 includes a plurality of pixels P. The pixels P emit light corresponding to a received data voltage.

Figure 2:
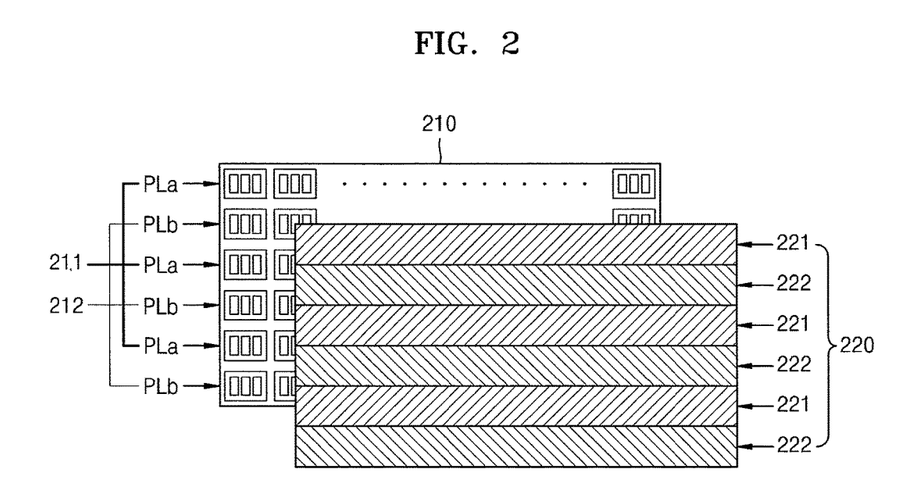
FIG. 2 is a schematic view illustrating a structure of a display unit according to an embodiment.

The display unit 200 includes a pixel unit 210 (see FIG. 2) and a polarization layer 220 (see FIG. 2). The pixel unit 210 and the polarization layer 220 will be described with reference to FIG. 2.

The source driver 300 receives an output image signal including image information, from among an output signal transmitted by using the control unit 100. The source driver 300 applies a data voltage to the pixels P of the display unit 200 based on the received output image signal.

The gate driver 400 receives a signal for adjusting an output timing of an image, from among an output signal transmitted by using the control unit 100. The gate driver 400 transmits a control signal for controlling the pixels P of the display unit 200 to the display unit 200 based on the received signal.

The power supply unit 500 receives a signal related to power from among output signals transmitted by using the control unit 100. The received signal can be supplied to the display unit 200. The power supply unit 500 applies power needed to drive the display unit 200 based on the received signal to the display unit 200.

In FIG. 1, the control unit 100, the source driver 300, the gate driver 400, and the power supply unit 500 are illustrated as separate blocks. However, all or some of the control unit 100, the source driver 300, the gate driver 400, and the power supply unit 500 can be implemented as separate integrated circuits or a single integrated circuit.

FIG. 2 is a schematic view illustrating a structure of a display unit according to an embodiment.

Referring to FIG. 2, the display unit 200 according to the present embodiment includes a pixel unit 210 and a polarization layer 220. The pixel unit 210 includes a first display area 211 and a second display area 212. The polarization layer 220 includes a first polarization layer 221 and a second polarization layer 222.

The pixel unit 210 is an area where the pixels P for displaying an image corresponding to a data voltage are formed. A data voltage is transmitted by using the control unit 100. The pixels P of the pixel unit 210 in FIG. 2 each include three subpixels SP. However, the embodiment is not limited thereto, and each pixel P can include one, two or three or more subpixels SP, or the pixels P can include different numbers of subpixels SP.

The pixels P of the pixel unit 210 can be formed of various elements that can emit light of different luminances or different wavelengths according to a data voltage, such as a liquid crystal device or an OLED.

The pixel unit 210 includes a plurality of pixel lines PLa and PLb each including a plurality of pixels. The pixel lines PLa and PLb are not physically divided lines but a set of pixels P arranged in a predetermined direction. For example, a set of pixels P located in a first row of the pixel unit 210 is one pixel line, and a set of pixels P located in a second row of the pixel unit 210 is another pixel line.

Although a set of the pixels P located in the same row is illustrated as a single pixel line in FIG. 2, the embodiment is not limited thereto, and a set of pixel P located in the same column can be regarded as a single pixel line.

In FIG. 2, a pixel line is illustrated as having a thickness corresponding to a pixel. However, the embodiment is not limited thereto, and a pixel line can also have a thickness corresponding to two or more pixels. For example, a set of pixels P located in a first row and pixels P located in a second row form one pixel line, and a set of pixels P located in a third row and pixels P located in a fourth row form another pixel line.

In FIG. 2, a pixel line is illustrated as including all pixels located in one entire row. However, the embodiment is not limited thereto. For example, the pixels P of the pixel unit 210 are divided into an area of a m-by-n matrix (that is, into m×n areas), and each area is a pixel line.

The first display area 211 includes some pixel lines PLa from among a plurality of pixel lines PLa and PLb. The second display area 212 includes pixel lines PLb not belonging to the first display area 211. For example, the plurality of pixel lines PLa and PLb are divided into pixel lines PLa located in odd-numbered rows and pixel lines PLb located in even-numbered rows. In this case, the first display area 211 can include pixel lines PLa located in the odd-numbered rows. Also, the second display area 212 can include pixel lines PLb located in the even-numbered rows.

In FIG. 2, the pixel lines PLa located in the odd-numbered rows are illustrated as being included in the first display area 211, and the pixel lines PLb located in the even-numbered rows are illustrated as being included in the second display area 212. However, the embodiment is not limited thereto. For example, pixel lines located in even-numbered rows are included in the first display area 211, and pixel lines located in odd-numbered rows are included in the second display area 212. According to another exemplary embodiment, pixel lines that are located in rows numbered corresponding to multiples of 3 are included in the second display area 212, and pixel lines located in rows other than those numbered corresponding multiples of 3 are included in the first display area 211.

The first display area 211 displays a first image. The first image is generated from an input image signal. The first image is an image in a visible light range that can be visible to a display user.

A first image signal is a signal included in an output image signal output by using the control unit 100. The first image signal includes image information needed to display a first image on the first display area 211. The first image signal is output by using the control unit 100 and is input to the source driver 300. The source driver 300 receives the first image signal and applies a data voltage to a pixel P included in the first display area 211 such that the first image is displayed on the first display area 211.

The second display area 212 displays a second image. The second image is one of a light therapy image and an image adjusted for color blindness.

A second image signal is a signal included in an output image signal output by using the control unit 100. The second image signal includes image information needed to display a second image on the second display area 212. The second image signal is output by using the control unit 100 and is input to the source driver 300. The source driver 300 receives the second image signal and applies a data voltage to a pixel P included in the second display area 212 such that the second image is displayed on the second display area 212.

The first and second display areas 211 and 212 can be physically separate devices or logically separate regions in a single device.

The polarization layer 220 includes a first polarization layer 221 having a first polarization direction and a second polarization layer 222 having a second polarization direction. A transmission axis in the first polarization direction and a transmission axis in the second polarization direction are different from each other. For example, if the first polarization direction is a right-handed circular polarization direction, the second polarization direction is a left-handed circular polarization direction that is opposite to the first polarization direction. Alternatively, if the first polarization direction is a linear polarization direction, the second polarization direction is a linear polarization direction that is orthogonal to a transmission axis of the first polarization direction.

The first polarization layer 221 is attached to the first display area 211. The first polarization layer 221 can be attached to the first display area 211 such that the first polarization layer 221 is in physical contact with the first display area 211, or a light-transmissive material can be interposed between the first polarization layer 221 and the first display area 211 to attach the first polarization layer 221 to the first display area 211.

The second polarization layer 222 is attached to the second display area 212. The second polarization layer 222 can be physically contacted to the second display area 212 to be attached to the second display area 212, or a light-transmissive material can be interposed between the second polarization layer 222 and the second display area 212 to attach the second polarization layer 222 to the second display area 212.

The first polarization layer 221 and the second polarization layer 222 can include various elements such as a Polaroid film or a polarizing plate, that can transmit light having a predetermined polarization direction from among incident light.

The first polarization layer 221 and the second polarization layer 222 can be physically separate devices or logically separate regions in one polarization layer 220.

Although line segments are illustrated in the first polarization layer 221 and the second polarization layer 222 in FIG. 2, the line segments do not actually exist in the first and second polarization layers 221 and 222 nor the line segments indicate polarization directions of either the first polarization layer 221 or the second polarization layer 222. Rather, the line segments are merely used for indicating positions of the first polarization layer 221 and the second polarization layer 222.

A first image is displayed on the first display area 211. Light representing the first image is emitted after passing through the first polarization layer 221. Thus, light emitted through the first display area 211 has a first polarization direction.

A second image is displayed on the second display area 212. Light indicating the second image is output after passing through the second polarization layer 222. Thus, light emitted through the second display area 212 has a second polarization direction.

Figure 3:
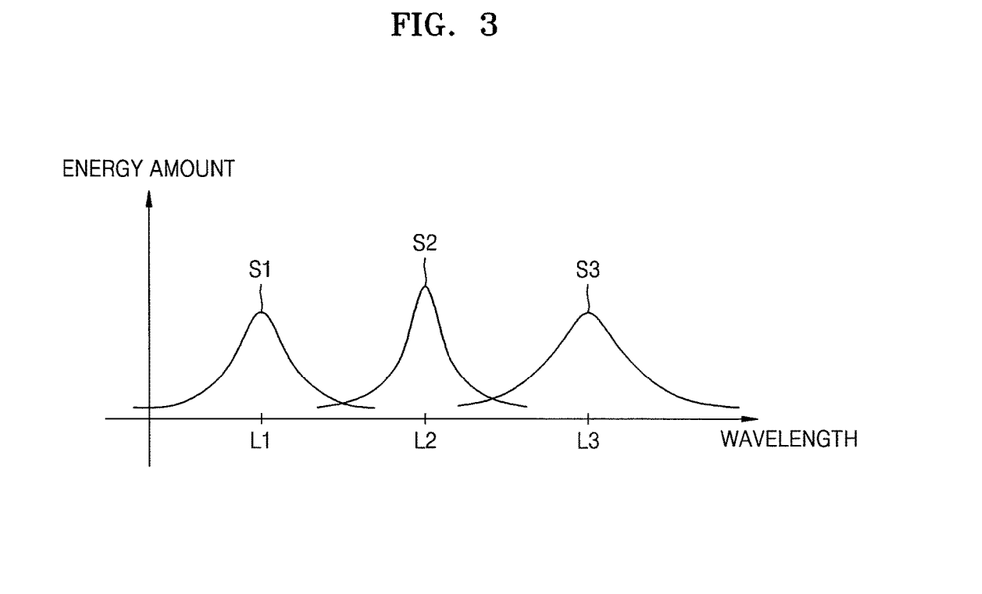
FIG. 3 is a schematic view illustrating an energy amount according to a wavelength of light for light therapy according to an embodiment.

FIG. 3 is a schematic view illustrating an energy amount according to a wavelength of light for light therapy according to an embodiment.

Referring to FIG. 3, the light for light therapy according to the present embodiment includes light of spectrums S1 through S3 within which peak energy is respectively output at particular wavelengths L1 through L3.

In general, a display area of a display device can emit visible light, and display of the emitted light on a display area is referred to as an image. However, in the present specification, a display area can emit infrared light or ultraviolet light, which are invisible to humans, and display of such invisible light emitted on a display area is also referred to as an image.

The wavelength L1 can be in a range of about 100 to about 380 nanometers, but is not limited thereto and can be in an ultraviolet wavelength range. The wavelength L2 can be about 490 to about 455 nanometers, but is not limited thereto and can be in a blue visible light range. The wavelength L3 can be in a range of about 800 to about 1000 nanometers, but is not limited thereto and can be in an infrared wavelength range.

Referring to FIG. 3, the spectrums S1, S2, and S3 are illustrated as energy spectrums corresponding to peak energy of light at different wavelengths, instead of as a single energy spectrum corresponding to peak energy of light at a single wavelength. However, the embodiment is not limited thereto, and the spectrums S1, S2, and S3 can be light emission spectrums from which energy is emitted only at a single wavelength.

If a second image is a light therapy image, the second image can be an image that is formed as light expressed by one of the spectrums S1, S2, and S3 and emitted through the second display area 212. For example, the second image is an image that is displayed as light having the peak energy at a wavelength of about 900 nanometers passing through and is emitted from the second display area 212. In this case, the second image is an image that is displayed as light having a peak energy in an infrared range is emitted through the second display area 212.

Light that includes at least one of light having a peak energy in an infrared range, light having a peak energy in an ultraviolet range, and light having a peak energy in a blue wavelength range can be beneficial to skin care, biorhythm control, depression treatment, inflammation treatment, or treatment of cancer. For example, light having the peak energy in a blue wavelength range is beneficial to skin care.

A light therapy image can include at least one of light for skin care, light for biorhythm control, light for depression treatment, light for inflammation treatment, and light for treatment of cancer. From among light for skin care, light for biorhythm control, light for depression treatment, light for inflammation treatment, and light for treatment of cancer, the control unit 100 can output, according to a type of light to be emitted through the second display area 212, a second image signal such that light that is expressed by one of the spectrums S1, S2, and S3 is emitted through the second display area 212. For example, light for skin care is output through the second display area 212. In this case, if it is assumed that light expressed by the spectrum S2 is beneficial to skin care, the light expressed by the spectrum S2 is to be emitted through the second display area 212. Thus, in order that the light expressed by the spectrum S2 is emitted through the second display area 212, the control unit 100 can output a second image signal such that a second image corresponding to the light expressed by the spectrum S2 is displayed on the second display area 212.

Figure 4:
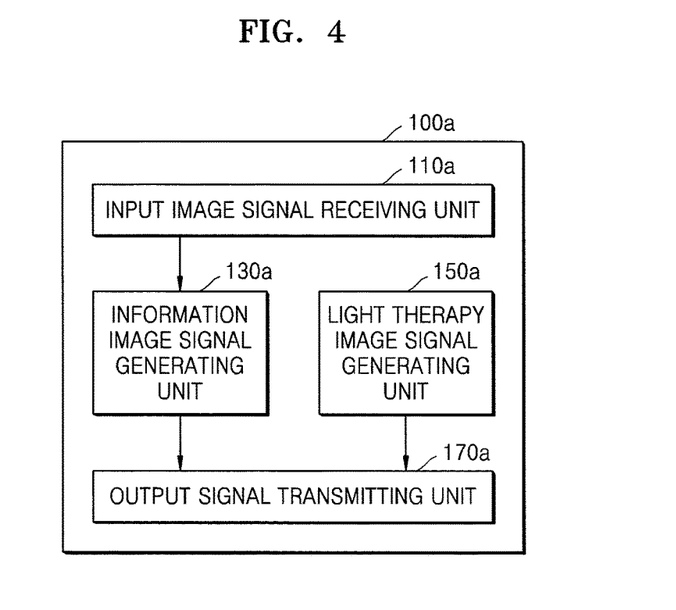
FIG. 4 is a schematic block diagram illustrating an operation of a control unit according to an embodiment.

FIG. 4 is a schematic block diagram illustrating an operation of a control unit 100a according to an embodiment.

Referring to FIG. 4, the control unit 100a according to the present embodiment includes an input image signal receiving unit or input image signal receiver 110a, an information image signal generating unit or information image signal generator 130a, a light therapy image signal generating unit or light therapy image signal generator 150a, and an output signal transmitting unit or output signal transmitter 170a.

The input image signal receiving unit 110a receives an input image signal transmitted from the outside of the display device 10.

The input image signal receiving unit 110a can include a regulator that adjusts a voltage of an input image signal. The input image signal receiving unit 110a can include a noise removing circuit that removes a noise signal included in an input image signal. The input image signal receiving unit 110a can include a protection circuit that prevents a reflow in a direction in which a signal is transmitted.

The input image signal receiving unit 110a can transmit a received input image signal to the information image signal generating unit 130a.

In some embodiments, the input image signal receiving unit 110a is not an additional integrated circuit but is included in an integrated circuit for implementing other elements included in the control unit 100a.

Although the input image signal receiving unit 110a is included in the control unit 100a in the present embodiment, the embodiments are not limited thereto and a unit that receives an input image signal can be included outside the control unit 100a.

The information image signal generating unit 130a generates a first image signal based on the input image signal received from the input image signal receiving unit 110a.

The information image signal generating unit 130a can generate a first image signal based on a proportion of the first display area 211 with respect to the pixel unit 210. For example, a first example in which a total of n pixels P are included in the first display area 211 and a second example in which a total of 2n pixels P are included in the first display area 211 are assumed. Both in the first example and the second example, in order to obtain identical or similar luminances of image frames displayed through the pixel unit 210, an average luminance of light emitted from the pixels P included in the first display area 211 in the first example must be about double an average luminance of light emitted from the pixels P included in the first display area 211 in the second example. In response to a first image signal generated by using the information image signal generating unit 130a, light output from each of the pixels P included in the first display area 211 in the first example can be brighter compared to light output from each of the 2n pixels P included in the first display area 211 in the second example.

The information image signal generating unit 130a can generate a first image signal based on a resolution of the first display area 211. For example, an input image signal is a signal including information about an image having a resolution of 1920×1080, and the pixel unit 210 can include pixels P in an arrangement of 1920×1080, and the first display area 211 can include pixels P in an arrangement of 1920×540. In this case, a first image signal for displaying the first image having a resolution of 1920×540 on the first display area 211 can be generated by using the information image signal generating unit 130a.

The information image signal generating unit 130a can generate the first image signal by using various signal processing methods.

The information image signal generating unit 130a can transmit the first image signal to the output signal transmitting unit 170a.

In some embodiments, the information image signal generating unit 130a is not an additional integrated circuit but is included in an integrated circuit for implementing other elements included in the control unit 100a.

Although the information image signal generating unit 130a is included in the control unit 100a in the present embodiment, the embodiments are not limited thereto and a unit that generates a first image signal can be included outside the control unit 100a.

The light therapy image generating unit 150a generates a second image signal such that light expressed by one of the spectrums S1, S2, and S3 of FIG. 3 is output through the second display area 212.

The light therapy image generating unit 150a can transmit the second image signal to the output signal transmitting unit 170a.

In some embodiments, the light therapy image generating unit 150a is not an additional integrated circuit but is included in an integrated circuit for implementing other elements included in the control unit 100a.

Although the light therapy image generating unit 150a is included in the control unit 100a in the present embodiment, the embodiments are not limited thereto, and a unit that generates a second image signal can be included outside the control unit 100a.

The output signal transmitting unit 170a can transmit the first image signal generated by using the information image signal generating unit 130a to the source driver 300. The output signal transmitting unit 170a can transmit the second image signal generated by using the light therapy image generating unit 150a to the source driver 300.

The output signal transmitting unit 170a can transmit a driving signal needed to display the first and second images through the display unit 200 to the gate driver 400. The output signal transmitting unit 170a can transmit a signal needed to control a power supply to the power supply unit 500.

The output signal transmitting unit 170a can include a regulator to adjust a voltage of an output image signal and a protection circuit to prevent a reflow in a direction in which a signal is transmitted.

The output signal transmitting unit 170a can be not an additional integrated circuit but included in an integrated circuit for implementing other elements included in the control unit 100a.

Although the output signal transmitting unit 170a is included in the control unit 100a in the present embodiment, the embodiments are not limited thereto, and a unit that generates an output signal can be included outside the control unit 100a.

While the input image signal receiving unit 110a, the information image signal generating unit 130a, the light therapy image generating unit 150a, and the output signal transmitting unit 170a are illustrated as separate blocks, all or some of the elements can be implemented as separate integrated circuits or can be implemented as a single integrated circuit.

Figure 5:
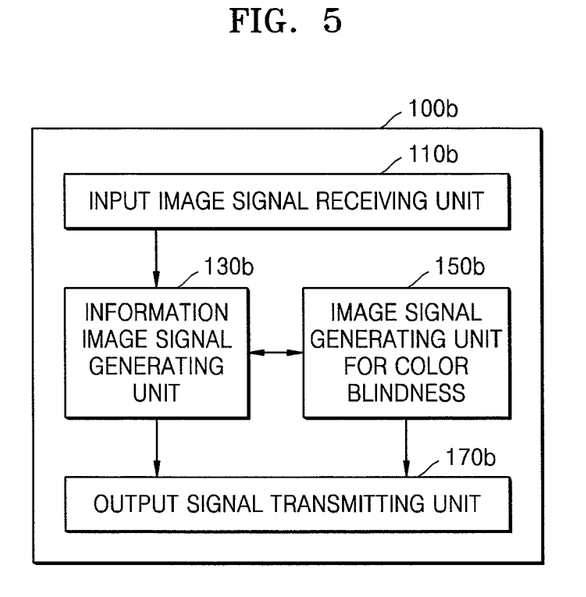
FIG. 5 is a schematic block diagram illustrating an operation of a control unit according to another embodiment.

FIG. 5 is a schematic block diagram illustrating an operation of a control unit 100b according to another embodiment.

Referring to FIG. 5, the control unit 100b according to the present embodiment includes an input image signal receiving unit or input image signal receiver 110b, an information image signal generating unit information image signal generator 130b, an image signal generating unit or image signal generator 150b for color blindness (or color blindness image signal generator), and an output signal transmitting unit or output signal transmitter 170b.

The input image signal receiving unit 110b receives an input image signal that is transmitted from the outside of the display device 10 and is input to the display device 10. The input image signal receiving unit 110b of FIG. 5 corresponds to the input image signal receiving unit 110a of FIG. 4 described above, and detailed description thereof will be omitted.

The information image signal generating unit 130b generates a first image signal based on an input image signal received from the input image signal receiving unit 110b. The information image signal generating unit 130b of FIG. 5 corresponds to the information image signal generating unit 130a of FIG. 4 described above, and detailed description thereof will be omitted.

The image signal generating unit 150b generates a second image signal based on at least one of the input image signal received from the input image signal receiving unit 110b and the first image signal.

Based on a selection made by a user, the image signal generating unit 150b can generate a second image signal, which allows for a second image in which at least one color among red, green, and blue is emphasized compared to the remaining colors, to be displayed by the second display area 212. The image signal generating unit 150b can generate a second image signal by using various signal processing methods.

The image signal generating unit 150b can generate a second image signal based on a proportion of the second display area 212 with respect to the pixel unit 210. For example, a first example in which a total of n pixels P are included in the second display area 212 and a second example in which a total of 2n pixels P are included in the second display area 212 are assumed. Both in the first and second examples, in order for luminances of image frames displayed through the pixel unit 210 are identical or similar, an average luminance of light emitted through each of the pixels P included in the second display area 212 in the first example is to be about twice higher than an average luminance of light emitted through each of the pixels P included in the second display area 212. The image signal generating unit 150b can generate a second image signal such that brighter light is output from each of the pixels P included in the second display area 212 in the first example than in the second example.

The image signal generating unit 150b can generate a second image signal based on a resolution of the second display area 212. For example, an input image signal is a signal for displaying an image having a resolution of 1920×1080, and the pixel unit 210 includes pixels P in an arrangement of 1920×1080, and the second display area 212 includes pixels P in an arrangement of 1920×540. In this case, a second image signal for displaying an image adjusted for color blindness, having a resolution of 1920×540 is generated by using the image signal generating unit 150b.

The image signal generating unit 150b can generate the second image signal by using various signal processing methods.

The image signal generating unit 150b can transmit the second image signal to the output signal transmitting unit 170b.

In some embodiments, the image signal generating unit 150b is not an additional integrated circuit but included in an integrated circuit for implementing other elements included in the control unit 100b.

Although the image signal generating unit 150b is included in the control unit 100b in the present embodiment, the embodiments are not limited thereto, and a unit that generates a second image signal can be included outside the control unit 100b.

The output signal transmitting unit 170b can transmit the first image signal generated by using the information image signal generating unit 130b to the source driver 300. The output signal transmitting unit 170a can transmit the second image signal generated by using the image signal generating unit 150b to the source driver 300.

The output signal transmitting unit 170b can transmit a driving signal needed to display the first image and the second image through the display unit 200 to the gate driver 400. The output signal transmitting unit 170b can transmit a signal needed to control a power supply to the power supply unit 500.

The output signal transmitting unit 170b can include a regulator that adjusts a voltage of an output image signal. The output signal transmitting unit 170b can include a protection circuit that prevents a reflow in a direction in which a signal is transmitted.

In some embodiments, output signal transmitting unit 170b is not an additional integrated circuit but is included in an integrated circuit for implementing other elements included in the control unit 100b.

Although the output signal transmitting unit 170b is included in the control unit 100b in the present embodiment, the embodiments are not limited thereto, and a unit that generates an output signal can be included outside the control unit 100b.

While the input image signal receiving unit 110b, the information image signal generating unit 130b, the image signal generating unit 150b, and the output signal transmitting unit 170b are illustrated as separate blocks, all or some of the elements can be implemented as separate integrated circuits or can be implemented as a single integrated circuit.

Figure 6A:
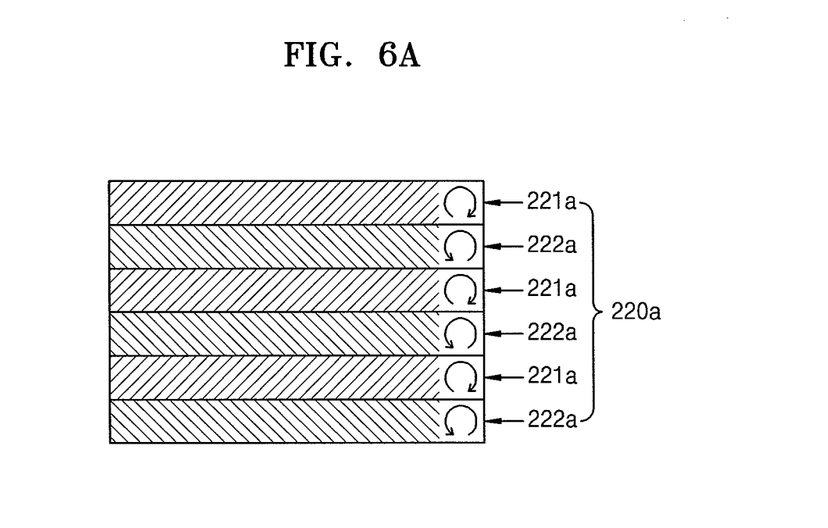
FIGS. 6A and 6B are views for describing a polarization layer having different polarization directions.
Figure 6B:
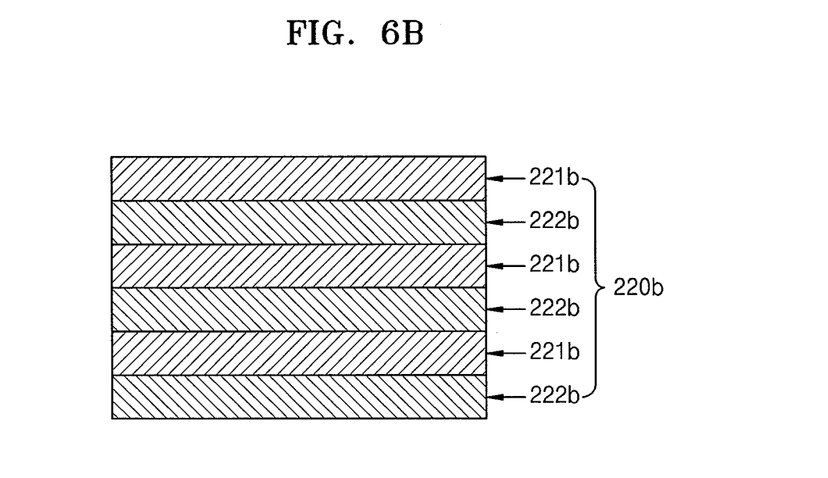

FIGS. 6A and 6B are views for describing a polarization layer having different polarization directions.

Referring to FIG. 6A, a polarization layer 220a includes a first polarization layer 221a having a first polarization direction which is a right-handed circular polarization direction or a left-handed circular polarization direction and a second polarization layer 222a that is a different circular polarization direction. For example, if the first polarization direction is a right-handed circular polarization direction, the second polarization direction is a left-handed circular polarization direction.

Referring to FIG. 6A, a right-handed circular polarization direction is denoted by an arrow rotating clockwise. While FIG. 6A illustrates line segments that extend from a right upper end to a left lower end in the first polarization layer 221a, the line segments do not actually exist in the first polarization layer 221a nor the line segments indicate a linear polarization direction. Rather, the line segments are merely used to indicate a position of the first polarization layer 221a having a right-handed circular polarization direction.

Referring to FIG. 6A, a left-handed circular polarization direction is denoted by an arrow rotating counterclockwise. While FIG. 6A illustrates line segments that extend from a left upper end to a right lower end in the second polarization layer 222a, the line segments do not actually exist in the second polarization layer 222a nor the line segments indicate a linear polarization direction. Rather, the line segments are merely used to indicate a position of the second polarization layer 221a having a left-handed circular polarization direction.

Referring to FIG. 6B, the polarization layer 222b according to another embodiment includes a first polarization layer 221b having a first polarization direction which is a straight line direction and a second polarization layer 222b having a second polarization direction which is a straight line direction substantially orthogonal to the first polarization direction. For example, if the first polarization direction is substantially parallel a horizontal line, the second polarization direction is substantially perpendicular to the horizontal line.

Although the first and second polarization layers 221b and 222b include line segments in FIG. 6B, no line segments actually exist in the first and second polarization layers 221b and 222b, and the line segments are used to indicate positions of the first and second polarization layers 221b and 222b.

While two examples of the polarization layer 220 having different polarization directions are described with reference to FIGS. 6A and 6B, the embodiments are not limited thereto, and various pairs of different polarization directions can be provided.

Figure 7:
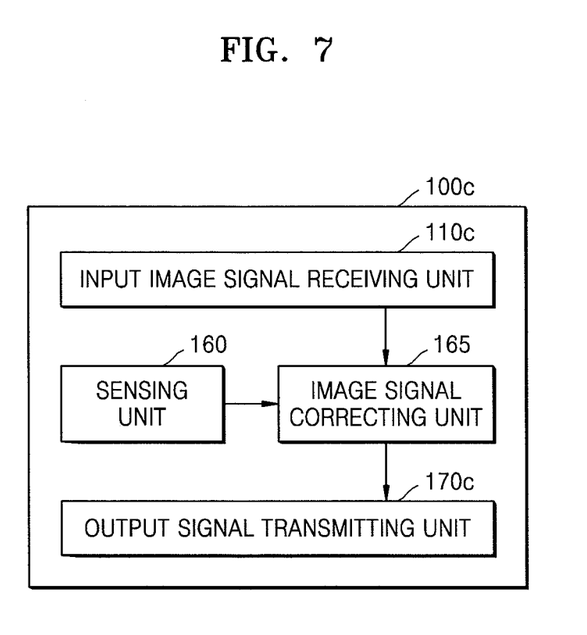
FIG. 7 is a schematic block diagram illustrating an operation of a control unit when using the polarization layer of FIG. 6B, according to an embodiment.

FIG. 7 is a schematic block diagram illustrating an operation of a control unit or controller 100c when using the polarization layer 220b of FIG. 6B, according to an embodiment.

Referring to FIG. 7, the control unit 100c includes an input image signal receiving unit or input image signal receiver 110c, a sensing unit or sensor 160, an image signal correcting unit or image signal corrector 165, and an output signal transmitting unit or output signal transmitter 170c.

The input image signal receiving unit 110c receives an input image signal that is transmitted from the outside of the display device 10 and is input to the display device 10. The input image signal receiving unit 110c of FIG. 7 corresponds to the input image signal receiving unit 110a of FIG. 4, and a repeated detailed description thereof will be omitted.

The control unit 100c can include an information image signal generating unit (not shown). The information image signal generating unit (not shown) included in the control unit 100c corresponds to the information image signal generating unit 130a of FIG. 4 described above, and a repeated detailed description thereof will be omitted.

The control unit 100c can include one of a light therapy image signal generating unit (not shown) and a image signal generating unit for color blindness (not shown). The light therapy image signal generating unit (not shown) corresponds to the light therapy image signal generating unit 150a of FIG. 4 described above, and a repeated detailed description thereof will be omitted. The image signal generating unit for color blindness (not shown) included in the control unit 100c corresponds to the image signal generating unit 150b of FIG. 5, and a repeated detailed description thereof will be omitted.

The sensing unit 160 senses a tilt angle of a user's head with respect to the display. An algorithm whereby the sensing unit 160 senses the tilt angle of the user's head with respect to the display can vary and can be at least one of a recognition algorithm regarding positions of a viewer's eyes and a recognition algorithm regarding a position of a viewer's head. The sensing unit 160 can transmit a determination result to the image signal correcting unit 165.

The image signal correcting unit 165 corrects first and second image signals, based on the tilt angle of the user's head with respect to the display, received from the sensing unit 160.

When the second image signal is a light therapy image signal, the image signal correcting unit 165 can correct the first image signal such that luminance of the first image increases as the tilt angle of the user's head increases. The image signal correcting unit 165 can correct the first image signal by using various signal processing methods.

By adjusting the luminance of the image signal to increase as the tilt angle of the user's head increases, the user who is wearing an eyeglass device can view the display device 10 without sensing any noticeable change in the luminance of the first image signal. An operation of a display system formed of a display device and an eyeglass device will be described with reference to FIGS. 8 and 9.

When the second image signal is a light therapy image signal, the image signal correcting unit 165 can correct the second image signal such that the second image is not displayed through the second display area if the tilt angle of the user's head exceeds a critical value. For example, if the tilt angle of the user's head exceeds about 10 degrees, the second image signal is corrected such that the second image is not displayed through the second display area. The image signal correcting unit 165 can correct the second image signal by using various signal processing methods.

If the tilt angle of the head of the user exceeds a predetermined critical value, the second image is adjusted to not be displayed through the second display area so that the user can view the display device 10 while light emitted through the second display area does not enter the two eyes of the user who is wearing an eyeglass device. An operation of the display system formed of a display device and an eyeglass device will be described with reference to FIGS. 8 and 9.

The image signal correcting unit 165 can transmit the corrected first image signal and the corrected second image signal to the output signal transmitting unit 170c.

The output signal transmitting unit 170c can transmit the first image signal generated by using the image signal correcting unit 165 to the source driver 300. The output signal transmitting unit 170c can transmit the second image signal generated by using the image signal correcting unit 165 to the source driver 300.

The output signal transmitting unit 170c can transmit a driving signal needed to display a first image and a second image through the display unit 200 to the gate driver 400.

The output signal transmitting unit 170c can transmit a signal needed to control a power supply to the power supply unit 500.

The output signal transmitting unit 170c can include a regulator that adjusts a voltage of an output image signal. The output signal transmitting unit 170c can include a protection circuit that prevents a reflow in a direction in which a signal is transmitted.

In some embodiments, the output signal transmitting unit 170c is not an additional integrated circuit but is included in an integrated circuit for implementing other elements included in the control unit 100a.

Although the output signal transmitting unit 170c is included in the control unit 100c in the present embodiment, the embodiments are not limited thereto, and a unit that receives an input image signal can be included outside the control unit 100c.

The input image signal receiving unit 110c, the sensing unit 160, the image signal correcting unit 165, and the output signal transmitting unit 170c are illustrated as separate blocks in FIG. 7. However, all or some of input image signal receiving unit 110c, the sensing unit 160, the image signal correcting unit 165, and the output signal transmitting unit 170c can be implemented as separate integrated circuits or a single integrated circuit.

Figure 8:
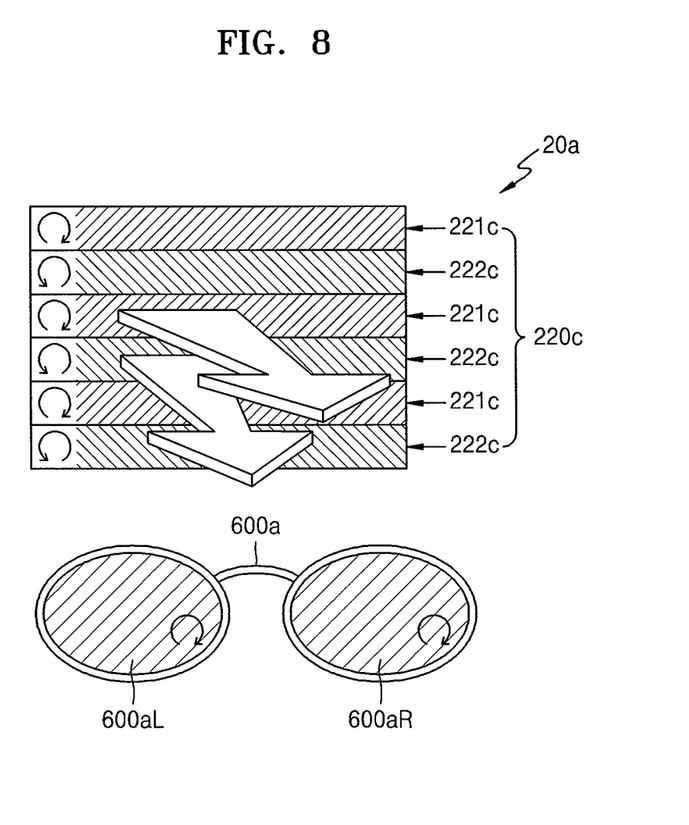
FIG. 8 is a schematic view illustrating a display system according to an embodiment.

FIG. 8 is a schematic view illustrating a display system 20a according to an embodiment.

Referring to FIG. 8, the display system 20a includes a polarization layer 220c and a first eyeglass device 600a.

Only the polarization layer 220c is illustrated in FIG. 8 for convenience in order to describe an operation of the display system 20a according to a polarization direction of the polarization layer 220c and a polarization direction of a lens of the first eyeglass device 600a; the polarization layer 220c is included in the display device 10 according to FIG. 1, and the display system 20a includes the display device 10 of FIG. 1 and the first eyeglass device 600a.

The polarization layer 220c includes a first polarization layer 221c and a second polarization layer 222c. The first polarization layer 221c has a first polarization direction, and the second polarization layer 222c has a second polarization direction. Light of the first polarization direction is emitted after passing through the first polarization layer 221c. Light of the second polarization direction is emitted after passing through the second polarization layer 222c.

The second image signal according to the embodiment of FIG. 8 is a light therapy image signal.

A left lens 600aL and a right lens 600aR of the first eyeglass device 600a include a polarization layer of a third polarization direction.

The third polarization direction can be the same as the first polarization direction. In this case, light that is emitted from the first display area 211 and passes through the first polarization layer 221c can then be transmitted through the left and right lenses 600aL and 600aR such that the light emitted from the first display area 211 reaches both eyes of the user who is wearing the first eyeglass device 600a. Accordingly, a first image can reach the two eyes of the user for receiving an information image signal. However, the second image can be prevented from being transmitted through the left lens 600aL and the right lens 600aR of the first eyeglass device 600a. Accordingly, the second image (i.e., a light therapy image) is prevented from reaching the two eyes, and thus, the eyes are not affected by the light therapy image.

Referring to FIG. 8, the first and third polarization directions are both right-handed circular polarization directions, and the second polarization direction is a left-handed circular polarization direction. However, the embodiment is not limited thereto, and polarization directions can vary. For example, the first and third polarization directions can be substantially identical, and the first and second polarization directions can be different from each other.

Figure 9:
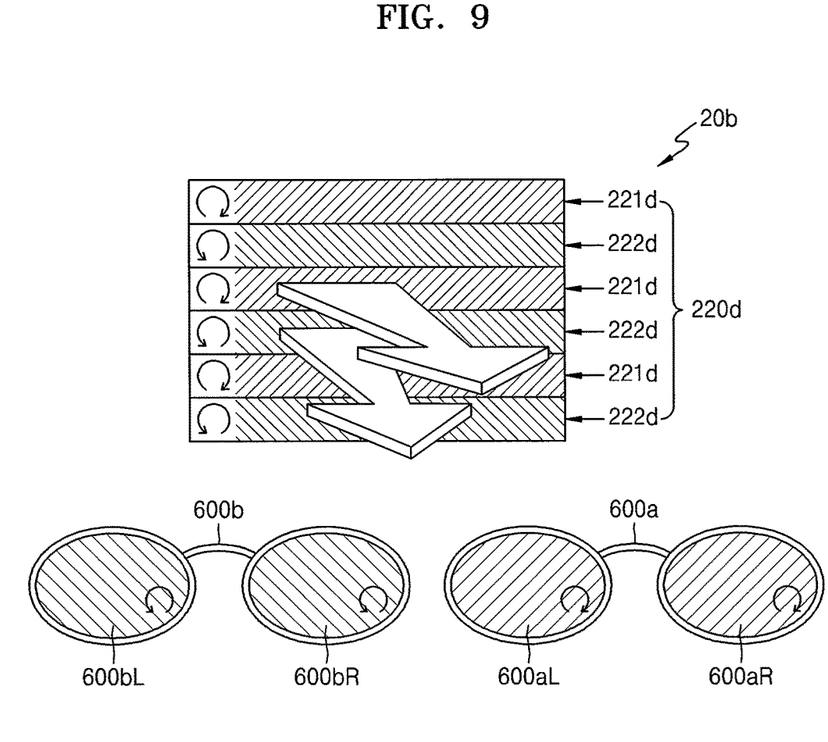
FIG. 9 is a schematic view illustrating a display system according to another embodiment.

FIG. 9 is a schematic view illustrating a display system 20b according to another embodiment.

Referring to FIG. 9, the display system 20b according to the other embodiment includes a polarization layer 220d, a first eyeglass device 600a, and a second eyeglass device 600b.

Only the polarization layer 220d is illustrated in FIG. 9 for convenience in order to describe an operation of the display system 20b according to a polarization direction of the polarization layer 220d and a polarization direction of a lens of the first eyeglass device 600a; the polarization layer 220d is included in the display device 10 according to FIG. 1, and the display system 20b includes the display device 10 of FIG. 1 and the first eyeglass device 600a and the second eyeglass device 600b.

The polarization layer 220d includes a first polarization layer 221d and a second polarization layer 222d. The first polarization layer 221d has a first polarization direction, and the second polarization layer 222d has a second polarization direction. A first image signal is output after passing through the first polarization layer 221d. A second image signal is output after passing through the second polarization layer 222d.

The second image signal according to the embodiment of FIG. 9 is an image signal adjusted for color blindness.

The left lens 600aL and the right lens 600aR of the first eyeglass device 600a include a polarization layer of a third polarization direction.

The third polarization direction can be the same as the first polarization direction. In this case, light that is emitted from the first display area 211 and passes through the first polarization layer 221d can then be transmitted through the left lens 600aL and the right lens 600aR such that the light emitted from the first display area 211 reaches both eyes. Accordingly, a first image can reach the two eyes of the user for receiving an information image signal. However, the second image can be prevented from being transmitted through the left lens 600aL and the right lens 600aR of the first eyeglass device 600a. Accordingly, the second image (i.e., an image adjusted for color blindness) is prevented from reaching the eyes, and thus, the eyes of the user are not affected by the image adjusted for color blindness.

A left lens 600bL and a right lens 600bR of the second eyeglass device 600b include a polarization layer of a fourth polarization direction.

The fourth polarization direction can be substantially the same as the second polarization direction. In this case, light that is emitted from the second display area 212 and passes through the first polarization layer 222d can then be transmitted through the left lens 600bL and the right lens 600bR such that the light emitted through the second display area 212 reaches both eyes of the user. Accordingly, the second image can reach the two eyes of the user who is wearing the second eyeglass device 600b for receiving an image signal adjusted for color blindness. However, the first image can be prevented from being transmitted through the left lens 600bL and the right lens 600bR of the second eyeglass device 600b. Accordingly, the first image (i.e., an image that is not adjusted for color blindness) is prevented from reaching the eyes of the user who is wearing the second eyeglass device 600b, and thus the eyes of the user are not affected by the image that is not adjusted for color blindness.

Referring to FIG. 9, the first and third polarization directions are both right-handed circular polarization directions, and the second and fourth polarization directions are both a left-handed circular polarization direction. However, the embodiment is not limited thereto, and polarization directions can vary such that the first and third polarization directions are the same polarization direction, the second and fourth polarization directions are the same polarization direction, and the first and second polarization directions are different directions.

According to one or more of the disclosed embodiments, light therapy can be performed while a display user views an information image. Also, a light therapy image signal is prevented from affecting the eyes of a display user.

Furthermore, a color blind person and a person who is not color blind can view an image at the same time.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While the inventive technology has been described with reference to the figures, it will be understood by those of ordinary skill in the art that various changes in form and details can be made therein without departing from the spirit and scope as defined by the following claims.

What is claimed is:

1. A display device comprising:
   a pixel unit including a first display area and a second display area;
   a controller configured to control the pixel unit to display a first image in the first display area and control the pixel unit to emit light having a peak energy in one of an infrared range and an ultraviolet range, which are in an invisible light range, through the second display area, wherein the first image is an image in a visible light range;
   a first polarization layer formed over the first display area and having a first polarization direction; and
   a second polarization layer formed over the second display area and having a second polarization direction different from the first polarization direction.

2. The display device of claim 1, wherein the pixel unit comprises a plurality of pixel lines including odd-numbered and even-numbered pixel lines, wherein each pixel line includes a plurality of pixels,
   wherein the first display area comprises one of a first area where the odd-numbered pixel lines are located and a second area where the even-numbered pixel lines are located, and
   wherein the second display area comprises the other of the first area and the second area.

3. The display device of claim 1, wherein the controller comprises an information image signal generator configured to generate a first image signal based at least in part on an input image signal received from an external device, and wherein the pixel unit is further configured to display the first image based on the first image signal.

4. The display device of claim 3, wherein the information image signal generator is further configured to generate the first image signal based at least in part on a ratio of the first display area to the area of the pixel unit.

5. The display device of claim 3, wherein the information image signal generator is further configured to generate the first image signal based at least in part on a resolution of the first display area.

6. The display device of claim 1, wherein the first polarization direction is one of a right-handed circular polarization direction or a left-handed circular polarization direction, and
   wherein the second polarization direction is the other circular polarization direction.

7. The display device of claim 1, further comprising a sensor configured to sense a tilt angle of the head of a user with respect to the display device,
   wherein the first polarization direction is a first linear polarization direction, and
   wherein the second polarization direction is a second linear polarization direction substantially orthogonal to the first linear polarization direction.

8. The display device of claim 7, wherein the controller further comprises:
   an information image signal generator configured to generate a first image signal adapted to a resolution of the first display area, based at least in part on an input image signal received from an external device; and
   an image signal corrector configured to correct the first image signal and an intensity of the light emitted through the second display area based at least in part on the tilt angle,
   wherein the pixel unit is further configured to display the first image based on the corrected first image signal and to emit the light having the corrected intensity.

9. The display device of claim 8, wherein the image signal corrector is further configured to increase the luminance of light emitted by each pixel in the first display area as the tilt angle increases.

10. The display device of claim 8, wherein the image signal corrector is further configured not to emit the light through the second display area if the tilt angle exceeds a critical angle.

11. The display device of claim 1, wherein the pixel unit comprises a plurality of pixel lines including odd-numbered pixel lines and even-numbered pixel lines, wherein each pixel line includes a plurality of pixels, wherein the first display area comprises the odd-numbered pixel lines configured to output the image in the visible light range, and wherein the second display area comprises the even-numbered pixel lines configured to output invisible light.

12. A display system comprising:
    a display device comprising:
       a pixel unit including a first display area and a second display area;
       a controller configured to control the pixel unit to display a first image for a first user in the first display area and control the pixel unit to display a second image for a second user with color blindness in the second display area, wherein the second image includes an image adjusted for color blindness;
       a first polarization layer formed over the first display area and having a first polarization direction; and
       a second polarization layer formed over the second display area and having a second polarization direction different from the first polarization direction;
    a first eyeglass device comprising left and right lenses, wherein both of the left and right lenses comprise a third polarization layer having the first polarization direction such that light emitted from the second display area does not enter eyes of the second user wearing the first eyeglass device; and a second eyeglass device comprising left and right lenses, wherein both of the left and right lenses of the second eyeglass device comprise a fourth polarization layer having the second polarization direction such that light emitted from the first display area does not enter eyes of the first user wearing the second eyeglass device.

13. The display system of claim 12, wherein the controller comprises an information image signal generator configured to generate a first image signal adapted to a resolution of the first display area based at least in part on an input image signal received from an external device, and wherein the pixel unit is further configured to display the first image based on the first image signal.

14. The display system of claim 13, further comprising a color blindness image signal generator configured to generate a second image signal adapted to a resolution of the second display area based at least in part on the first image signal, wherein the pixel unit is further configured to display the second image based on the second image signal, and wherein the resolution of the second display area is same as the resolution of the first display area.

15. The display system of claim 14, wherein the second image includes an image in which at least one of green, red and blue colors is emphasized compared to the remaining color(s) based at least in part on a type of the color blindness of the second user of the display device.

16. A display device comprising:
a display panel including odd-numbered and even-numbered pixel lines each comprising a plurality of pixels, wherein the display panel is configured to display a first image through the odd-numbered pixel lines and configured to emit light having a peak energy in one of an infrared range and an ultraviolet range, which are in an invisible light range, through the even-numbered pixel lines, wherein the first image is an image in a visible light range;

a controller comprising an information image signal generator configured to generate a first image signal based at least in part on an input image signal received from an external device, wherein the display panel is further configured to display the first image based on the first image signal;

a first polarization layer formed over the odd-numbered pixel lines and having a first polarization direction; and a second polarization layer formed over the even-numbered pixel lines and having a second polarization direction different from the first polarization direction.

17. The display device of claim 16, further comprising a sensor configured to sense a tilt angle of the head of a user with respect to the display device,
wherein the first polarization direction is a first linear polarization direction,
wherein the second polarization direction is a second linear polarization direction substantially orthogonal to the first linear polarization direction, and
wherein the controller further comprises an image signal corrector configured to correct the first image signal displayed through the odd-numbered pixel lines and an intensity of the light emitted through the even-numbered pixel lines based at least in part on the tilt angle.

* * * * *